United States Patent [19]

Hofer et al.

[11] 4,042,690

[45] Aug. 16, 1977

[54] METHOD OF COMBATTING BLOWFLY LARVAE

[75] Inventors: Wolfgang Hofer; Fritz Maurer; Hans-Jochem Riebel; Wilhelm Stendel, all of Wuppertal-Elberfeld, Germany

[73] Assignee: Bayer Aktiengesellschaft, Germany

[21] Appl. No.: 710,680

[22] Filed: Aug. 2, 1976

[30] Foreign Application Priority Data

Aug. 22, 1975 Germany .............................. 2537486

[51] Int. Cl.$^2$ ............................................. A61K 31/675
[52] U.S. Cl. .................................................... 424/200
[58] Field of Search ................................. 424/250, 200

[56] References Cited

U.S. PATENT DOCUMENTS 2,759,937  8/1956  Breuil .................................... 424/200

*Primary Examiner*—Sam Rosen
*Attorney, Agent, or Firm*—Jacobs & Jacobs

[57] ABSTRACT

Ectoparasiticidal compositions and uses employing 0,0-dialkyl-0-pyridazine phosphoric and thionophosphoric acid esters are described. A typical embodiment is a composition for combatting blowflies containing diethyl-0-[1-phenyl-6-oxopyridazin-3-yl]phosphoric acid ester.

5 Claims, No Drawings

METHOD OF COMBATTING BLOWFLY LARVAE

The present invention relates to the use of known O,O-dialkyl-O-pyridazine(thiono)-phosphoric acid esters as ectoparasiticides in the veterinary medicine field.

The use of the known O,O-dialkyl-O-pyridazine(thiono)-phosphoric acid esters as insecticides in the plant protection field has already been disclosed (compare U.S. Pat. No. 2,759,937).

Further, it has already been disclosed that certain O,O-dialkyl-O-pyrimidinethionophosphoric acid esters, especially O,O-diethyl-O-[2-iso-propyl-6-methyl-pyrimidin(4)-yl]-thionophosphoric acid ester, exhibit insecticidal properties (compare U.S. Pat. No. 2,754,243). Thus O,O-diethyl-O-[2-iso-propyl-6-methyl-pyrimidin(4)-yl]-thionophosphoric acid ester, in particular, can be used to kill larvae of *Lucilia cuprina*. However, the action of this compound is not satisfactory if low amounts are used.

It has been found that the known O,O-dialkyl-O-pyridazine(thiono)-phosphoric acid esters of the formula

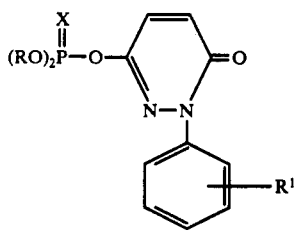

(I)

in which
R represents alkyl with 1 to 4 carbon atoms,
R¹ represents hydrogen or nitro and
X represents oxygen or sulphur exhibit powerful ectoparasiticidal properties.

It is surprising that the O,O-dialkyl-O-pyridazine(thiono)-phosphoric acid esters which can be employed according to the invention are outstandingly suitable for use against ectoparasites in the veterinary medicine field and have a substantially greater action against ectoparasites than the previously known compounds of the same type of action. Thus, inter alia, blowfly larvae have, in certain areas, become resistant to the phosphoric acid ester derivatives hitherto employed to combat them, so that the success in combating them is, in many areas, dubious. For example, the Goondiwindi strain of Lucilia cuprina has become highly resistant to phosphoric acid ester derivatives. The O,O-dialkyl-O-pyridazine-(thiono)-phosphoric acid esters which can be used according to the invention, on the other hand, have an excellent action against the abovementioned resistant pests, whilst being very well tolerated by warm-blooded animals.

The compounds which can be used according to the invention thus represent a genuine enrichment of the art.

The O,O-dialkyl-O-pyridazine(thiono)-phosphoric acid esters to be used according to the invention are accurately defined the formula (I) and are already known as insecticides in the plant protection field (compare U.S. Pat. No. 2,759,937). However, their use as ectoparasiticides in the veterinary medicine field is new.

Preferably, in the formula (I),

R represents straight-chain or branched alkyl with 1 to 3 carbon atoms,
R¹ represents hydrogen and
X represents sulphur.

The following may be mentioned individually as examples of the active compounds according to the invention: O,O-dimethyl-O-[1-phenyl-6-oxo-pyridazin(3)yl]-phosphoric acid ester, O,O-dimethyl-O-[1-phenyl-6-oxo-pyridazin(3)yl]-thionophosphoric acid ester, O,O-diethyl-O-[1-phenyl-6-oxo-pyriadzin(3)yl]-phosphoric acid ester, O,O-diethyl-O-[1-phenyl-6-oxopyridazin(3-)yl[ -thionosphophoric acid ester, O,O-di-n-propyl-O-[1-phenyl-6-oxo-pyridazin(3)yl]-phosphoric acid ester, O,O-di-n-propyl-O-[1-phenyl-6-oxo-pyridazin(3)yl]-thionophosphoric acid ester, O,O-di-iso-propyl-O-[1-phenyl-6-oxo-pyridazin(3)yl]-phosphoric acid ester, O,O-di-iso-propyl-O-[1-phenyl-6-oxo-pyridazin(3)yl]-thionophosphoric acid ester, O,O-dimethyl-O-[1-p-nitrophenyl-6-oxo-pyridazin(3)yl]-phosphoric acid ester, O,O-dimethyl-O-[1-p-nitrophenyl-6-oxo-pyridazin(3)yl]-thionophosphoric acid ester, O,O-diethyl-O-[1-p-nitrophenyl-6-oxo-pyridazin(3)yl]-phosphoric acid ester, O,O-diethyl-O-[1-p-nitrophenyl-6-oxo-pyridazin(3)yl]-thionophosphoric acid ester, O,O-di-n-propyl-O-[1-p-nitrophenyl-6-oxo-pyridazin(3)yl]-phosphoric acid ester, O,O-di-n-propyl-O-[1-p-nitrophenyl-6-oxo-pyridazin(3)yl]-thionophosphoric acid ester, O,O-di-iso-propyl-O-[1-p-nitrophenyl-6-oxo-pyridazin(3)yl]-phosphoric acid ester and O,O-di-iso-propyl-O-[1-p-nitrophenyl-6-oxo-pyridazin(3)yl]-thionophosphoric acid ester.

The active compounds according to the invention possess a good biocidal activity, especially an ectoparasiticidal activity, whilst being of low toxicity to warm-blooded animals.

In the veterinary medicine field, the active compounds according to the invention are employed successfully against numerous harmful animal parasites (preferably ectoparasites from the class of the Arachnida and the class of the Insecta).

The following may be mentioned as ectoparasites from the classs of the Insecta: Diptera, such as, for example, the sheep ked (*Melophagus ovinus*) and Diptera larvae which are parasitic in warm-blooded animals, such as, for example, *Lucilia cuprina, Lucilia sericata* and *Chrysomia chloropyga* and larvae of warble flies, such as, for example, the ox warble fly (*Hypoderma bovis*).

In the course of time, parasitic fly larvae and ticks have, in many areas, become resistant to the preparations hitherto employed as pesticides, so that the success in combating them is, in many areas, becoming increasingly dubious. To ensure economic livestock husbandry in the infested areas, there is an urgent requirement for agents by means of which these parasites can be combated reliably. For example, in Australia the Goondiwindi strain of *Lucilia cuprina* is highly resistant to the phosphoric acid ester agents used hitherto. The active compounds according to the invention are equally effective against both the normally sensitive and the resistant strains, for example of Lucilia. When applied in the usual manner they have, in the host animal, a direct destructive effect on all forms which are parasitic on the animal, so that the development cycle is interrupted in the parasitic phase on the animal.

Within the class of the Insecta, the following may furthermore be mentioned as ectoparasites:

from the order Phthiraptera, Menoponidae such as, for example, *Menopon gallinae* and *Eomenacanthus stramineus*, Trichodectidae such as, for example, *Trichodectes canis*, Bovicolidae, such as, for example *Bovicola bovis*, Haematopinidae, such as, for example, *Haematopinus suis* and *Haematopinus eurysternum*, and Linognathidae such as, for example, *Linognathus vituli*.

From the order Diptera, Tabanidae, such as, for example, *Tabanus ovinus*, Muscidae, such as, for example *Musca autumnalis, Stomoxys calcitrans* and *Lyperosia irritans*, Calliphoridae, such as, for example, *Lucilia sericata* and *Lucilia cuprina, Chrysomya chlorophyga, Chrysomya bezziana* and *Callitroga hominivorax*, Cuteribridae, such as, for example, *Dermatobia hominis*, Oestridae, such as, for example, *Oestrus ovis, Hypoderma bovis* and *Hypoderma lineatum*, Gasterophilidae, such as, for example, *Gastrophilus haemorrhoidalis* and Hippoboscidae, such as, for example, *Melophagus ovinus* and *Hippobosca equina*.

From the order Siphonaptera, Pulicidae, such as, for example, *Ctenocephalides canis* and Ctenocephalides felis, and Ceratophyllidae, such as, for example, *Ceratophyllus gallinae*.

The compounds according to the invention are especially effective against blowfly larvae, and in particular also against blowfly larvae which are restistant to phosphoric acid ester derivatives, such as, for example, the highly resistant Goondiwindi strain of *Lucilia cuprina*.

In the veterinary field, the active compounds according to the invention are employed in known manner, preferably by dermal or topical use, for example in the form of dipping, spraying, pour-on and spot-on, and powdering, and by parenteral use, for example in the form of an injection. In the present case, dermal use is preferred.

The formulations are prepared in a known manner, for example by extending the active compounds with solvents and/or carriers, if appropriate using emulsifiers and/or dispersing agents; if, for example, water is used as the diluent, organic solvents can, if appropriate, be used as auxiliary solvents.

The following may be mentioned as auxiliaries: water and non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol); solid excipients, such as, for example, natural rock powders (for example kaolins, alumina, talc and chalk), synthetic rock powders (for example highly disperse silica and silicates) and sugars (for example raw sugar, lactose and glucose); emulsifiers, such as non-ionic and anionic emulsifiers (for example polyoxyethylene-fatty acid esters, polyoxyethylene-fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

The active compounds according to the invention are generally present in the formulations in concentrations of 0.1 to 95 percent by weight, preferably 0.5 to 90 percent by weight. Preparations which are intended for direct application contain the active compound according to the invention in concentrations of between 0.001 and 5 percent by weight, preferably 0.005 to 3 percent by weight.

Where the active compounds are applied by powdering, spraying, pouring or atomising, or as a bath (dip), yet further auxiliaries and/or active compounds, such as insecticides or disinfectants, may be admixed to the formulations, or the ready-to-use solutions, in addition to the customary solid or liquid extenders, diluents and/or surface-active agents.

The new active compounds can be employed in the usual manner. Preferably, they are applied dermally, but parenteral, especially subcutaneous, application and oral application are also possible.

In general, it has proved advantageous to administer amounts of about 1 to about 100 mg of the new compounds per kg of body weight per day in order to achieve effective results.

Nevertheless it can at times be necessary to deviate from the amounts mentioned, and in particular to do so in accordance with the body weight of the test animal and/or the method of application, but also because of the species of animal and its individual behavior towards the medicament, or the nature of the formulation of the latter and the time or interval at which it is administered. Thus it can suffice in some cases to manage with less than the above mentioned minimum amount while in other cases the upper limit mentioned must be exceeded. Where substantial amounts are applied, it can be advisable to divide these into several individual administrations over the course of the day. The general sense of the other statements made above also applies.

The action of the active compounds according to the invention against various parasites will be illustrated in more detail with the aid of the use examples which follow:

EXAMPLE A

Parasitic Fly Larvae Test

Solvent: 35 parts by weight of ethylene glycol monomethyl ether 35 parts by weight of nonylphenol polyglycol ether.

To produce a suitable preparation of active compound, 30 parts by weight of the active substance in question is mixed with the stated amount of solvent, which contains the abovementioned proportion of emulsifier, and the concentrate thus obtained is diluted with water to the desired concentration.

About 20 fly larvae (*Lucilia cuprina*) are introduced into a test tube which contains about 2 cm³ of horse muscle. 0.5 ml of the active compound preparation is applied to this horsemeat. After 24 hours, the degree of destruction in % is determined 100% means that all larvae have been killed and 0% that none of the larvae have been killed.

| Active compounds according to the present application | Active compound concentration in ppm | Destructive action in per cent, Lucilia cuprina resistant |
|---|---|---|
| $(C_2H_5-O)_2P(=O)-O-\text{[pyridazinone ring with N-N-C}_6H_5\text{]}=O$ | 100 | 100 |
| | 30 | 100 |
| | 10 | 100 |
| | 3 | 100 |
| | 1 | 0 |

| Active compounds according to the present application | Active compound concentration in ppm | Destructive action in per cent, Lucilia cuprina resistant |
|---|---|---|
| (C₂H₅—O)₂P(S)—O—[pyridazinone-N-C₆H₅] | 100<br>30<br>10<br>3<br>1<br>0.3 | 100<br>100<br>100<br>100<br>100<br>0 |
| (C₂H₅—O)₂P(S)—O—[pyridazinone-N-(4-NO₂-C₆H₄)] | 100<br>10<br>1 | 100<br>>50<br>0 |

Active compound of a known agent:

| Active compounds according to the present application | Active compound concentration in ppm | Destructive action in per cent, Lucilia cuprina resistant |
|---|---|---|
| (C₂H₅—O)₂P(S)—O—[C(C₃H₇-iso)=N—N=C(CH₃)] | 100<br>30<br>10<br>3<br>1 | 100<br>100<br>100<br>>50<br>0 |

What is claimed is:

1. The method of combatting infestation of animals by blowfly larvae which comprises applying to the infested animal a blowfly larvae biocidal amount of a compound of the formula:

$$\begin{array}{c} RO \\ \phantom{RO}\diagdown \\ \phantom{RO}PO \\ RO \diagup \end{array} \overset{X}{\underset{\|}{\phantom{P}}} -O-\underset{N-N}{\overset{\phantom{O}}{\bigcirc}}=O \quad \text{with phenyl-}R^1$$

wherein
R is alkyl of 1 to 4 carbon atoms;
R¹ is hydrogen or nitro; and
X is oxygen or sulfur.

2. The method according to claim 1 wherein the amount applied daily is from about 1 to about 100 mg per kg of body weight.

3. The method according to claim 1 wherein R is ethyl, R¹ is hydrogen and X is oxygen.

4. The method according to claim 1 wherein R is ethyl, R¹ is hydrogen and X is sulfur.

5. The method according to claim 1 wherein R is ethyl, R¹ is 4-nitro and X is sulfur.

* * * * *